United States Patent [19]

Reuter et al.

[11] Patent Number: 4,994,579
[45] Date of Patent: Feb. 19, 1991

[54] AROMATIC ETHER IMIDES

[75] Inventors: Knud Reuter; Dieter Freitag, both of Krefeld; Günther Weymans, Leverkusen; Rolf Dhein, Krefeld, all of Fed. Rep. of Germany

[73] Assignee: Bayer Aktiengesellschaft, Leverkusen Bayerwerk, Fed. Rep. of Germany

[21] Appl. No.: 417,216

[22] Filed: Oct. 4, 1989

[30] Foreign Application Priority Data

Oct. 12, 1988 [DE] Fed. Rep. of Germany ....... 3834660

[51] Int. Cl.$^5$ ............................................ C07D 403/12
[52] U.S. Cl. .................................................... 548/461
[58] Field of Search ........................................ 548/461

[56] References Cited

U.S. PATENT DOCUMENTS

| | | |
|---|---|---|
| 3,833,544 | 9/1974 | Takekoshi et al. ............... 528/28 |
| 3,850,885 | 11/1974 | Takekoshi et al. ............... 528/170 |
| 3,875,116 | 4/1975 | Heath et al. ..................... 528/208 |
| 3,905,942 | 9/1975 | Takekoshi et al. ............... 528/179 |
| 3,998,840 | 12/1976 | Williams et al. ................. 548/462 |
| 4,011,198 | 3/1977 | Takekoshi et al. ............... 528/26 |
| 4,073,773 | 2/1978 | Banucci et al. ................... 528/208 |
| 4,324,882 | 4/1982 | Takekoshi ........................ 528/206 |
| 4,324,883 | 4/1982 | White et al. ...................... 528/207 |
| 4,324,884 | 4/1982 | White et al. ...................... 528/207 |
| 4,324,885 | 4/1982 | White et al. ...................... 528/207 |

Primary Examiner—Mary E. Ceperley
Attorney, Agent, or Firm—Joseph C. Gil; Aron Preis

[57] ABSTRACT

The new aromatic ether imides corresponding to the following formula

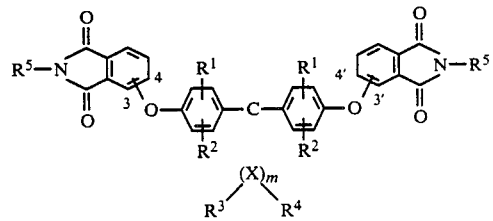

may be used for the production of plastics which in turn may be worked up into moulded articles, films, sheet products and filaments. The plastics produced from the new aromatic ether imides are distinguished by their exceptional dimensional stability under heat.

1 Claim, No Drawings

AROMATIC ETHER IMIDES

This invention relates to new aromatic ether imides, to a process for their preparation and to the use of the new aromatic ether imides for the production of plastics and plastic mixtures which can be worked up into moulded products, films, sheet products and filaments.

This invention relates to new aromatic ether imides corresponding to formula (I)

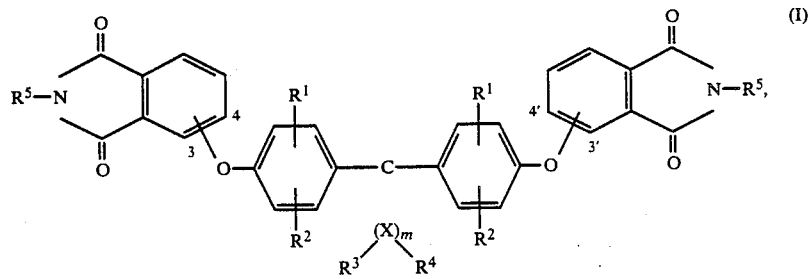

wherein $R^1$ and $R^2$ denote, independently of one another, hydrogen, halogen, $C_1$-$C_8$-alkyl, $C_5$-$C_6$-cycloalkyl, $C_6$-$C_{10}$-aryl or $C_7$-$C_{12}$-aralkyl, $R^3$ and $R^4$ may be different on each X and denote, independently of one another, hydrogen or $C_1$-$C_6$-alkyl, X denotes a carbon atom under the condition that at least one ring carbon atom is at the same time substituted by two $C_1$-$C_6$-alkyl groups, $R^5$ denotes $C_1$-$C_4$-alkyl, $C_5$-$C_6$-cycloalkyl or $C_6$-$C_{10}$-aryl, and m stands for an integer with a value from 4 to 7.

The halogens in the formulae shown above may be, for example, fluorine, chlorine or bromine, in particular bromine or chlorine, and the alkyl groups may be methyl, ethyl, propyl or butyl groups, preferably methyl groups; the cycloalkyl groups may be cyclopentyl or cyclohexyl groups, preferably cyclohexyl groups; the aryl groups may be phenyl or naphthyl groups, preferably phenyl groups, and the aralkyl groups may be benzyl or cumyl groups, preferably cumyl groups.

In the above formula, m stands for the integer 4 or 5, in particular the integer 5.

Compounds corresponding to the following formulae are preferred aromatic ether imides:

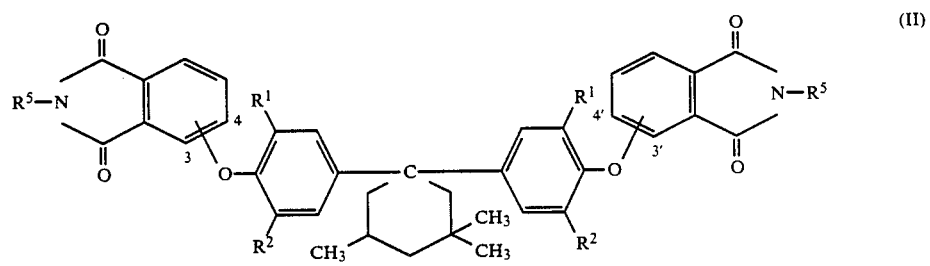

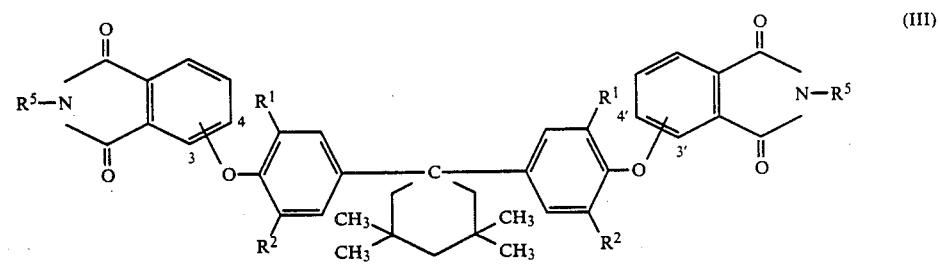

and

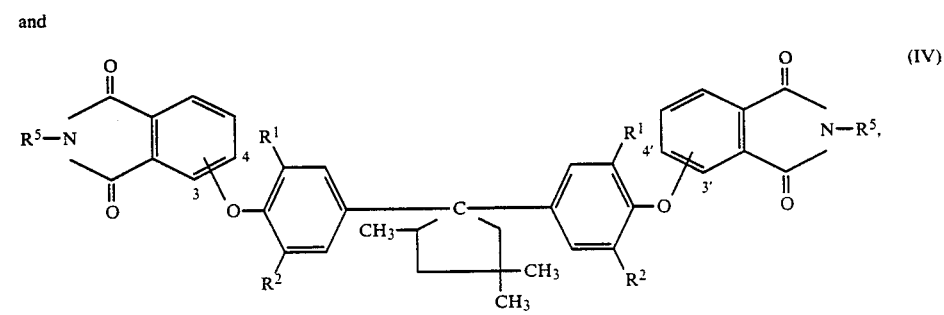

wherein $R^1$, $R^2$ and $R^5$ have the meanings mentioned for formula (I).

Aromatic ether imides of formula (II) in which the groups $R^1$ and $R^2$ are hydrogen or methyl, independently of one another, and $R^5$ stands for methyl or phenyl are particularly preferred, especially compounds of formula (II) in which $R^1$ and $R^2$ denote hydrogen and $R^5$ denotes methyl.

This invention further relates to a process for the preparation of aromatic ether imides corresponding to formula (I)

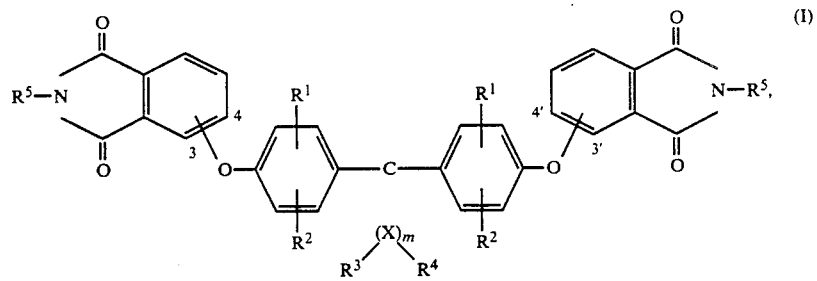

in which
$R^1$ and $R^2$ denote, independently of one another, hydrogen, halogen, $C_1$-$C_8$-alkyl, $C_5$-$C_6$-cycloalkyl, $C_6$-$C_{10}$-aryl or $C_7$-$C_{12}$-aralkyl,
$R^3$ and $R^4$ may be separately chosen for each X and denote, independently of one another, hydrogen or $C_1$-$C_6$-alkyl,
X stands for a carbon atom under the condition that at least one ring carbon atom is at the same time substituted by two $C_1$-$C_6$-alkyl groups,
$R^5$ denotes $C_1$-$C_4$-alkyl, $C_5$-$C_6$-cycloalkyl or $C_6$-$C_{10}$-aryl, and
m denotes an integer with a value from 4 to 7,
characterised in that compounds corresponding to formula (V)

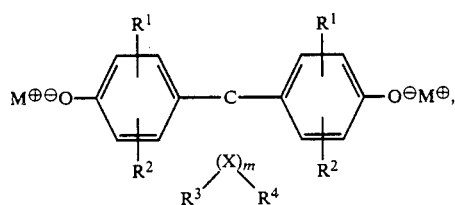

wherein
$R^1$, $R^2$, $R^3$, $R^4$, X and m have the meanings indicated above and
M denotes an alkali metal, in particular lithium, sodium or potassium,
are reacted with compounds corresponding to formula (VI)

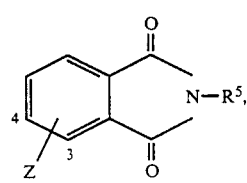

wherein
$R^5$ has the meaning indicated above and
Z denotes fluorine, chlorine, bromine, iodine or the nitro group, preferably nitro, fluorine or chlorine, most preferably nitro,
at temperatures from 20° to 180° C., preferably from 50° to 150° C., in the presence of a dipolar, aprotic solvent.

The compounds corresponding to formula (V) are put into the process in quantities of about 2 to 3 mol, preferably 2 to 2.5 mol, based on 1 mol of the compound of formula (VI).

The following are mentioned as preferred dipolar aprotic solvents: Acetonitrile, diethyleneglycol dimethylether, N,N-dimethylacetamide, N-methylpyrrolidone, N-methylcaprolactam, N,N-dimethylformamide and/or dimethylsulphoxide. Dimethylsulphoxide is particularly preferred. A proportion of the dipolar, aprotic solvents, preferably up to about 50% by weight thereof, may be replaced by apolar solvents such as toluene, xylene, mesitylene. chlorobenzene, cyclohexane and/or petroleum ether.

The quantity of solvent used may vary within a wide range. About 0.5 to 50 parts by weight of solvent, preferably 2 to 20 parts by weight of solvent, based on the total quantity of compounds of formula (V) and (VI) put into the process, are generally used; see U.S. Pat. No. 3,873,593 which gives details of the described process.

The compounds of formula (VI) put into the process are known and have been described, for example in Flitsch, Chem. Ber. 94, page 2498 (1961). Williams and Donahue, J. Org. Chem. 42, (21), pages 3414 et seq (1977), and Markezich and Zamek, J. Org. Chem. 42, (21), page 3431 (1977) or they may be prepared by the process described in U.S. Pat. No. 4,005,102.

The aromatic dihydroxy compounds corresponding to formula (V) may be prepared by condensation of the corresponding phenols in known manner with the corresponding ketones in the presence of acid catalysts and optionally cocatalysts. See in this connection German Patent Application No. P 38 32 396.6 and Schnell, Chemistry and Physics of Polycarbonates, Interscience Publishers, New York, 1964.

The following are examples of compounds corresponding to formula (V) which may be used in the process according to the invention:

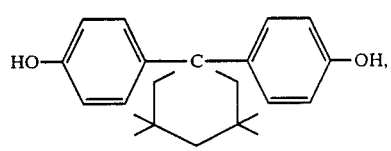

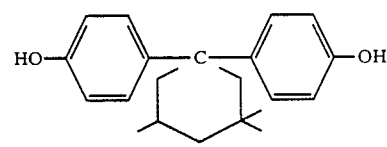

preferably

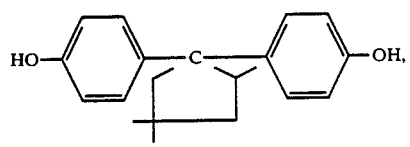

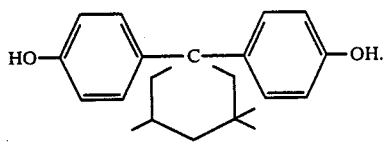

The following are examples of suitable compounds corresponding to formula (VI):

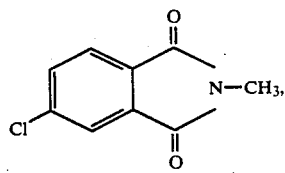

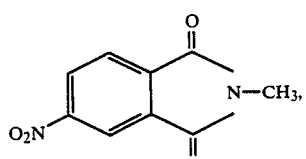

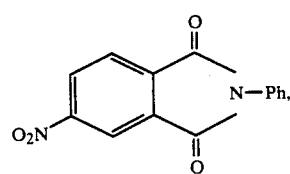

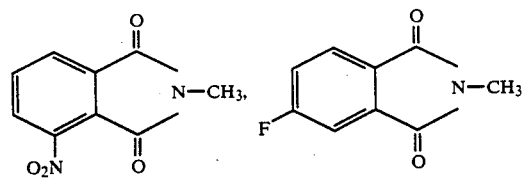

preferably

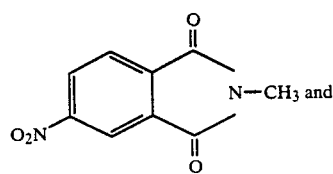

and

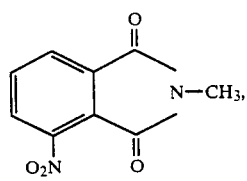

most preferably

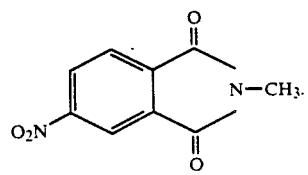

This invention further relates to the use of the new aromatic ether imides for the preparation of polymers, in particular duroplasts and thermoplasts. The polymers prepared from the new aromatic ethers may in turn be used for the production of moulded articles, films, filaments and sheet products.

The new aromatic ether imides may be used, for example, for the preparation of polyether imides, ether tetracarboxylic acids and ether tetracarboxylic acid dianhydrides.

The new aromatic ether imides or suitable secondary products obtained therefrom (ether carboxylic acids or ether carboxylic acid anhydrides) are polycondensed in the usual manner with the other comonomers suitable for the individual plastics. The polymers mentioned above may be prepared by processes known in the literature (see, for example, U.S. Pat. Nos. 3,833,544, 3,848,870, 3,850,885, 3,875,116, 3,905,942, 3,998,840, 4,011,198, 4,073,773, 4,324,884, 4,324,882, 4,324,885 and 4,324,883).

The ether imides according to the invention or their secondary products used for the production of the plastics (ether carboxylic acids, ether carboxylic acid anhydrides) may also be polycondensed with other suitable units, e.g. pyromellitic acid (dianhydride). Known ether imides and their secondary products such as those described in the above-mentioned U.S. Patent Specifications may also be used as part of the starting materials for polycondensation.

The polymers prepared from the new aromatic ether imides may, of course, also be mixed in the usual proportions and the usual manner with one another and with other known polymers, such as polycarbonates, polyester carbonates, polyesters, polyimides, polyamides, polyether ketones, polyether sulphones and/or aromatic polyethers.

The polymers prepared from the new aromatic ether imides have exceptionally high dimensional stability in the heat compared with comparable polymers based on known hydroxydiphenyl cycloalkanes.

EXAMPLES

Example 1

46.6 g of the bisphenol corresponding to the following formula:

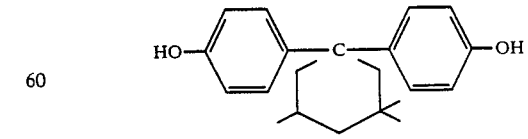

(0.15 M), 26.7 g of 45% NaOH (0.3 M), 200 ml of dimethylsulphoxide and 130 ml of toluene are refluxed under nitrogen in a stirrer apparatus with water separator until no more water separates. The water separator is then replaced by a Soxhlet apparatus fitted with a 4 Å molecular sieve and refluxing of the mixture is continued for a further hour. The Soxhlet apparatus is then replaced by a descending condensor and the mixture is distilled to a bottom temperature of 145° C., during which mainly toluene is removed.

68.3 g of 4-nitro-N-methylphthalimide (0.33 M) are then added and the reaction mixture is heated to 60° C. under nitrogen for 6 hours. After expiry of this reaction time and cooling to room temperature, 64.1 g of product are isolated by suction filtration and washed once with methanol and once with H₂O. After the mother liquor has been left to stand overnight, a further 13.3 g of product is isolated and washed with methanol and H₂O. Total yield: 77.4 g = 82% of theoretical yield. The product (both fractions) has a melting point of 201° to 203° C. and is identified by NMR spectroscopy and elemental analysis (C 74.5%, H 5.96%, N 4.67%, theoretical: C 74.5%, H 5.77%, N 4.46%) as a compound having the following structure:

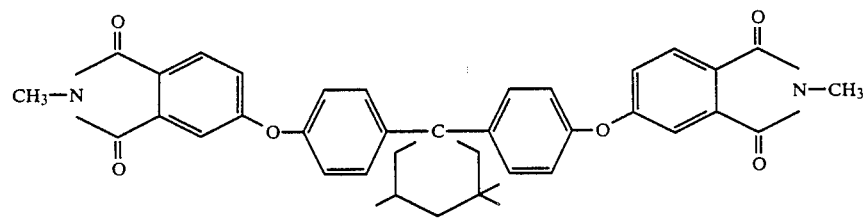

EXAMPLE 2

23.3 g of the bisphenol corresponding to the following formula

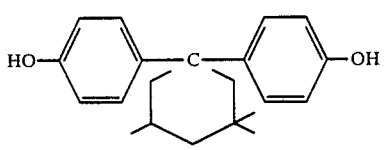

(prepared according to Example 1), 272.3 g of 45% NaOH, 200 ml of ethanol and 450 ml of H₂O are refluxed for 4½ hours. Then the solution is adjusted with H₂SO₄ to a pH value of 1 and the precipitate is washed with H₂O. The product is identified by its NMR spectrum and elemental analysis to be the tetracarboxylic acid:

(0.075 M), 13.35 g of 45% NaOH (0.15 M), 100 ml of dimethylsulphoxide, 65 ml of toluene and 34.15 g of 3-nitro-N-methylphthalimide (0.165 M) were reacted as in Example 1. After the product had been worked up as in Example 1, 39.0 g (83% of the theoretical yield) of the compound corresponding to the following formula

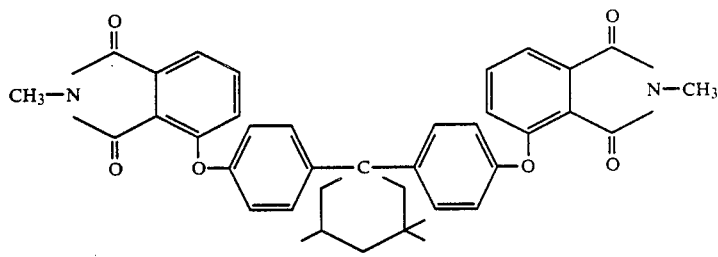

melting at 244°–245° C. were isolated and the structure as confirmed by NMR spectroscopy and elemental analysis:

|  | C | H | N |
|---|---|---|---|
| theoretical | 74.5 | 5.77 | 4.46% |
| found | 74.3 | 5.78 | 4.47% |

EXAMPLE 3

282.9 g of the bisimide

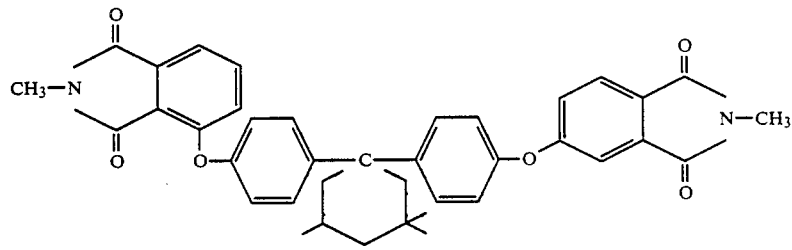

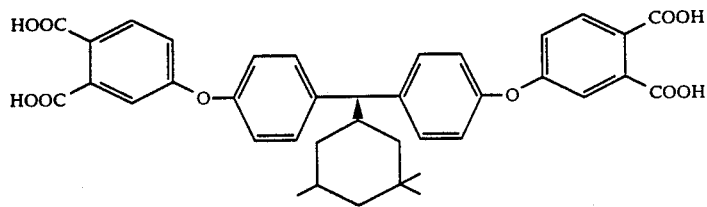

Elemental analaysis:

|  | C | H |
|---|---|---|
| theoretical | 69.6 | 5.37% |
| found | 70.3 | 5.20% |

EXAMPLE 4

107.6 g of the tetracarboxylic acid of Example 3 are refluxed in 357 g of acetic anhydride and the mixture is then filtered whilst hot. The mother liquor is distilled. The residue (83.2 g) is identified by its NMR spectrum, IR spectrum and elemental analysis to be the dianhydride:

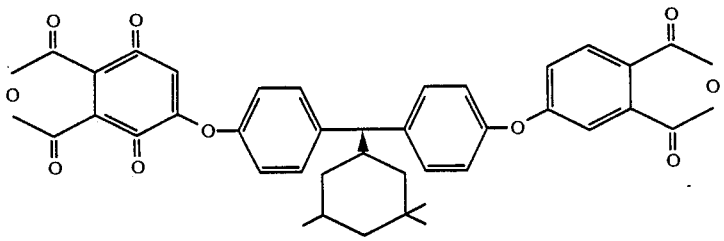

Elemental analysis:

|  | C | H |
|---|---|---|
| theoretical | 71.5 | 5.45% |
| found | 73.5 | 5.41% |

EXAMPLE 5

44.37 g of the dianhydride from Example 4, 8.65 g of m-phenylenediamine and 3.66 mg of sodium hypophosphite monohydrate were polycondensed in 96 g of o-dichlorobenzene for 10 hours under $N_2$.

The mixture was then diluted with 50 ml of $CH_2Cl_2$ and the polymer of the structure:

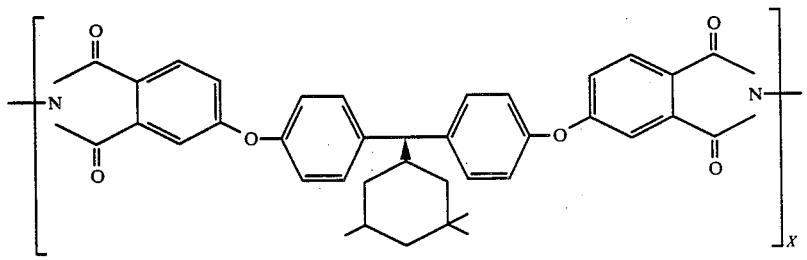

was isolated by precipitation in methanol.

We claim:

1. Aromatic ether imides corresponding to the following formula

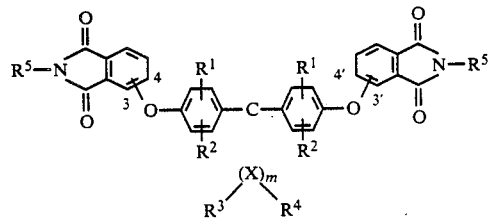

wherein $R^1$ and $R^2$ denote, independently of one another, hydrogen, halogen, $C_1$–$C_8$-alkyl, $C_5$–$C_6$-cycloalkyl, $C_6$–$C_{10}$-aryl or $C_7$–$C_{12}$-aralkyl, $R^3$ and $R^4$, which can be chosen individually for each X, denote, independently of one another, hydrogen or $C_1$–$C_6$-alkyl, X stands for carbon under the condition that at least one ring carbon atom is at the same time substituted by two $C_1$–$C_6$-alkyl groups, $R^5$ stands for $C_1$–$C_4$-alkyl, $C_5$–$C_6$-cycloalkyl or $C_6$–$C_{10}$-aryl, and m stands for an integer with a value from 4 to 7.

* * * * *